(12) United States Patent
Olson et al.

(10) Patent No.: US 8,390,438 B2
(45) Date of Patent: Mar. 5, 2013

(54) ROBOTIC CATHETER SYSTEM INCLUDING HAPTIC FEEDBACK

(75) Inventors: Eric S. Olson, Maplewood, MN (US); Mark B. Kirschenman, Waverly, MN (US); Troy T. Tegg, Elk River, MN (US); John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 866 days.

(21) Appl. No.: 12/507,175

(22) Filed: Jul. 22, 2009

(65) Prior Publication Data
US 2010/0073150 A1 Mar. 25, 2010

Related U.S. Application Data

(60) Provisional application No. 61/099,904, filed on Sep. 24, 2008.

(51) Int. Cl.
*H04B 3/36* (2006.01)
(52) U.S. Cl. ............... 340/407.1; 340/573.1; 340/4.11; 340/4.12; 340/4.1; 600/114; 600/146; 604/95.01; 604/95.04
(58) Field of Classification Search .............. 340/407.1, 340/573.1, 4.11, 4.12, 4.1; 600/407–411, 600/424, 114, 146; 604/95.1, 95.04
See application file for complete search history.

(56) References Cited

U.S. PATENT DOCUMENTS

| | | | |
|---|---|---|---|
| 5,607,462 A * | 3/1997 | Imran | 607/122 |
| 7,263,397 B2 | 8/2007 | Hauck et al. | |
| 2006/0293643 A1* | 12/2006 | Wallace et al. | 606/1 |
| 2007/0198008 A1* | 8/2007 | Hauck et al. | 606/41 |
| 2008/0009791 A1* | 1/2008 | Cohen et al. | 604/95.01 |
| 2009/0012533 A1* | 1/2009 | Barbagli et al. | 606/130 |
| 2009/0247993 A1* | 10/2009 | Kirschenman et al. | 606/1 |
| 2010/0256558 A1* | 10/2010 | Olson et al. | 604/95.01 |

* cited by examiner

*Primary Examiner* — Daryl Pope
(74) *Attorney, Agent, or Firm* — Dykema Gossett PLLC

(57) ABSTRACT

A haptic feedback system for a robotic catheter system including a robotic catheter manipulator assembly including one or more removably mounted robotic catheter device cartridges and robotic sheath device cartridges, with each cartridge being generally linearly movable relative to the robotic catheter manipulator assembly. The haptic feedback system may include a user interface device for controlling an operation associated with the catheter and/or sheath device cartridges, and a control system for evaluating a predetermined and/or a measured operational parameter of the haptic feedback system. The user interface device may provide haptic feedback to a user based on the evaluation by the control system.

33 Claims, 15 Drawing Sheets

ROBOTIC CATHETER SYSTEM INCLUDING HAPTIC FEEDBACK

CROSS REFERENCE TO RELATED APPLICATIONS

This application claims the benefit of priority to U.S. provisional application No. 61/099,904, filed 24 Sep. 2008 (the '904 application). The '904 application is hereby incorporated by reference as though fully set forth herein.

BACKGROUND OF THE INVENTION a. Field of the Invention

This invention relates to a robotic catheter system and method for automated control of a catheter and related components. In particular, the instant invention relates to a robotic catheter system providing haptic feedback during manipulation of a catheter and related components, for example, for diagnostic, therapeutic, mapping and ablative procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

One method of assisting a user with such treatment procedures includes the use of catheter based sensors for detecting force, contact, or proximity to the endocardial wall. For example, a user can view a graphical user interface to determine or confirm when an endocardial wall has been contacted or maneuver a catheter by viewing it relative to the vicinity of the endocardial wall. Such a method of information transmission is however limited in that a user's attention may be focused elsewhere. Further, when tissue contact sensing is combined with a robotic catheter system, where the catheter is being manipulated by a device such as a joystick or another controller, the normal mechanical feedback relayed to the user via the catheter shaft and handle can be lost.

The inventors herein have thus recognized a need for a system and method for precise and dynamic automated control of a catheter and its related components, for example, for diagnostic, therapeutic, mapping and ablative procedures, that will provide haptic feedback to a user in a variety of predetermined or user-specific forms, for assisting a user with a procedure, particularly with a robotic catheter system.

BRIEF SUMMARY OF THE INVENTION

A system and method for providing haptic feedback during manipulation of a catheter and related components, for example, for diagnostic, therapeutic, mapping and ablative procedures, may include a haptic feedback system for a robotic catheter system including a robotic catheter manipulator assembly including one or more removably mounted robotic catheter device cartridges and robotic sheath device cartridges, with each cartridge being generally linearly movable relative to the robotic catheter manipulator assembly. The haptic feedback system may include a user interface device for controlling an operation associated with the catheter and/or sheath device cartridges, and a control system for evaluating a predetermined and/or a measured operational parameter of the haptic feedback system. The user interface device may provide haptic feedback to a user based on the evaluation by the control system.

For the haptic feedback system described above, the user interface device may be an instrumented catheter handle control, an oversized catheter model, a user-wearable glove, a joystick, and/or a haptic spaceball (e.g. trackball). In an embodiment, the operational parameter may include a type, attachment, detachment, speed of movement and/or axial or angular positions of the catheter and/or sheath device cartridges relative to the manipulator assembly. The user interface device, in an embodiment, may be operatively connected to a catheter and sheath respectively connected to the catheter and sheath device cartridges. In an embodiment, the operational parameter may include a speed of movement, force, proximity, angle of attack and/or rotational orientation of the catheter and/or sheath relative to an endocardial wall. The endocardial wall, in an embodiment, may be computer generated. The operational parameter, in one embodiment, may include a tension of a steering wire for manipulating the catheter and/or sheath. In an embodiment, the operational parameter may be a temperature and/or texture of an endocardial wall relative to the catheter and/or sheath.

For the haptic feedback system described above, in an embodiment, the user interface device may be configured to provide virtual and/or augmented haptic feedback. In an embodiment, the virtual feedback may directly correlate to the operational parameter. In an embodiment, the augmented feedback may indirectly correlate to the operational parameter. The haptic feedback may include active resistance, active push, active pull, vibration, and/or temperature variation of the user interface device. In an embodiment, the haptic feedback may be user selectable. In an embodiment, a haptic type, mode and/or proportionality of the haptic feedback may be user selectable based on the specific cartridge type, or other parameters.

In an embodiment, a haptic feedback system for a robotic catheter system may include a robotic catheter manipulator assembly including one or more removably mounted robotic catheter device cartridges and robotic sheath device cartridges, with each cartridge being movable relative to the robotic catheter manipulator assembly. The haptic feedback system may include a user interface device for controlling an operation of the robotic catheter system, and a control system for evaluating a predetermined and/or a measured operational parameter of the haptic feedback system. The user interface device may provide haptic feedback to a user based on the evaluation by the control system.

In an embodiment, a method of providing haptic feedback for a robotic catheter system including a robotic catheter manipulator assembly including one or more removably mounted robotic catheter device cartridges and robotic sheath device cartridges, with each cartridge being generally linearly movable relative to the robotic catheter manipulator assembly. The method may include controlling an operation associated with the catheter and/or sheath device cartridges. The method may further include evaluating a predetermined and/or a measured operational parameter of the robotic catheter system, and providing haptic feedback to a user based on the evaluation.

For the method described above, in an embodiment, the operational parameter may include a type, attachment, detachment, speed of movement, and/or axial and/or angular positions of the catheter and/or sheath device cartridges relative to the manipulator assembly. In an embodiment, the operational parameter may include a speed of movement, force, proximity, angle of attack and/or rotational orientation of a catheter and/or sheath, respectively connected to the catheter and sheath device cartridges, relative to an endocardial wall. The endocardial wall, in an embodiment, may be computer generated. In an embodiment, the operational parameter may be a temperature and/or texture of an endocardial wall relative to a catheter and/or sheath respectively connected to the catheter and sheath device cartridges.

For the method described above, in an embodiment, the method may further include providing virtual and/or augmented haptic feedback. In an embodiment, the virtual feedback may directly correlate to the operational parameter. The augmented feedback, in an embodiment, may indirectly correlate to the operational parameter. In an embodiment, the haptic feedback may be user selectable.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
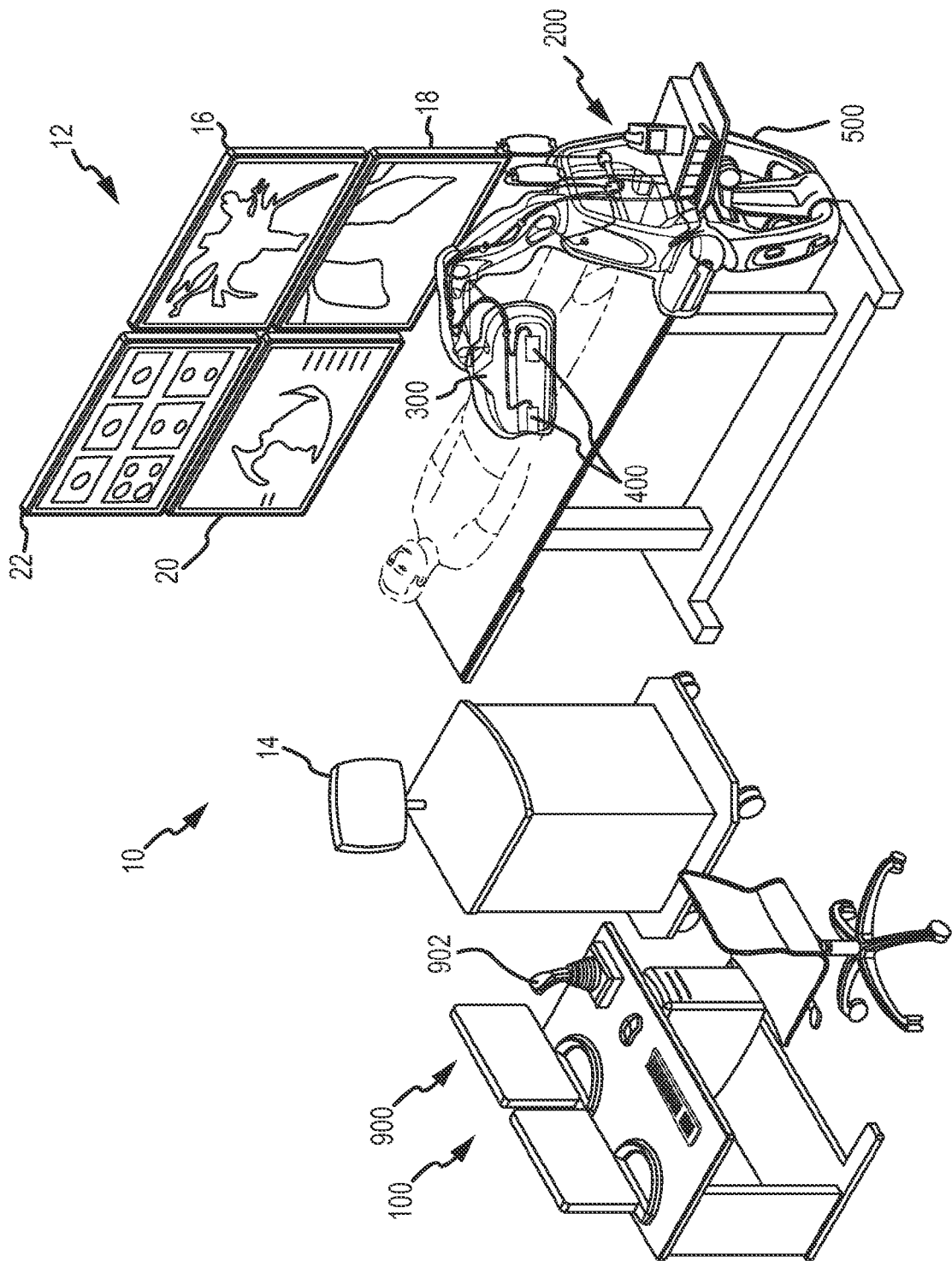
FIG. 1 is an isometric diagrammatic view of a robotic catheter system, illustrating an exemplary layout of various system components, including a haptic feedback system.
Figure 2:
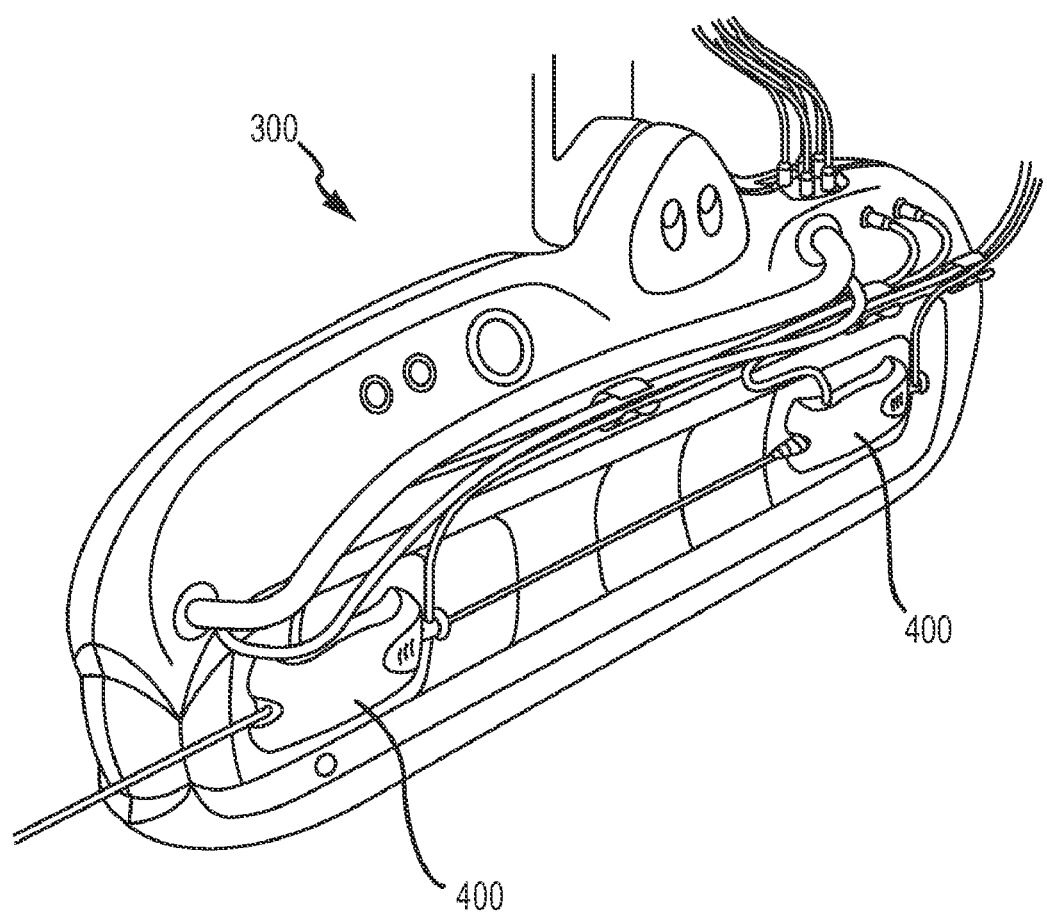
FIG. 2 is an enlarged isometric view of an exemplary robotic catheter manipulator assembly, also shown in FIG. 1.

Referring now to the drawings wherein like reference numerals are used to identify identical components in the various views, an embodiment of robotic catheter system 10 (described in detail in commonly owned and copending application titled "Robotic Catheter System"), also referred to as "the system," may be likened to "fly by wire" operation for a catheter system. The system may be used, for example, to manipulate the location and orientation of catheters and sheaths in a heart chamber or in another body cavity. As shown in FIG. 1, robotic catheter system 10 may generally incorporate a human input device and control system (referred to as "input control system") 100, e.g., a joystick and related controls (described in detail below and in commonly owned and copending application titled "Robotic Catheter System Input Device"), that a user such as an electrophysiologist (EP) may interact with, an electronic control system 200 (described in detail below and in commonly owned and copending application titled "Robotic Catheter System with Dynamic Response") that translates motions of the user at the input device into a resulting movement of a catheter tip, and a visualization system 12 that provides a user with real-time or near-real-time positioning information concerning the catheter tip. The system may further include closed-loop feedback using an EnSite NavX™ Navigation and Visualization system 14 and/or optical force transducers, a robotic catheter manipulator assembly 300 (described in detail in commonly owned and copending application titled "Robotic Catheter Manipulator Assembly") for operating a robotic catheter device cartridge 400 (described in detail in commonly owned and copending applications titled "Robotic Catheter Device Cartridge" and "Robotic Catheter Rotatable Device Cartridge"), and manipulator support structure 500 (described in detail in commonly owned and copending application titled "Robotic Catheter System"). The system may provide the user with a similar type of control provided by a conventional manual system, but allows for repeatable, precise, and dynamic movements with haptic feedback to a user during selected system operations by means of haptic feedback system 900, optionally integrated with input control system 100. The respective disclosures of the above-identified and other commonly owned and copending applications discussed in this application are incorporated herein by reference.

An embodiment of robotic catheter system 10 may involve automated catheter movement. A user, such as an EP, could identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then perform the desired treatment or therapy—which may further be in accordance with a defined algorithm. This system could enable full robotic control by using optimized path planning routines together with closed-loop position control. Furthermore, the system could automate certain "best-practices," such as pulling the catheter across the surface, or making contact at an oblique angle.

Referring to FIG. 1, input control system 100, described in further detail below, will be described briefly for a general introduction to robotic control system 10, and haptic feedback system 900.

Input control system 100, described below and in commonly owned and copending application titled "Robotic Catheter System Input Device," may generally allow a user to control the movement and advancement of both the catheter and sheath. Generally, several types of joysticks may be employed, including, without limitation, instrumented traditional catheter handle controls, oversized catheter models, instrumented, user-wearable gloves, and traditional joysticks. In embodiments, for example and without limitation, the joystick may be spring or motor centering so that any movement from the center position causes an incremental movement of the actual catheter tip, or the joystick may work in absolute terms. Haptic feedback system 900, as discussed in detail below, may also be incorporated to provide a user with a sense of when contact has been made, or during movement and other operations of the robotic catheter system.

Referring to FIG. 1, electronic control system 200 will be described briefly.

As discussed in detail in commonly owned and copending applications titled "Robotic Catheter System Input Device," and "Robotic Catheter System with Dynamic Response," many additional features may be included with embodiments of the system to, for example, improve the accuracy or effectiveness of the system. Such features may include, closed-loop feedback using EnSite NavX™ Navigation and Visualization system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

Visualization system 12 may provide a user with real-time or near-real-time positioning information concerning the catheter tip. In an exemplary embodiment, system 12 may include an EnSite NavX™ Navigation and Visualization monitor 16 for displaying cardiac chamber geometries or models, displaying activation timing and voltage data to identify arrhythmias, and for facilitating guidance of catheter movement. A fluoroscopy monitor 18 may be provided for displaying a real-time x-ray image or for assisting a physician with catheter movement. Additional exemplary displays may include an ICE and EP Pruka displays, 20, 22, respectively. Visualization system 12 may be integrated with haptic feedback system 900 as discussed below.

Referring to FIG. 1, EnSite NavX™ Navigation and Visualization system 14 will be described briefly.

EnSite NavX™ Navigation and Visualization system 14 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. System 14 may collect electrical data from catheters and use this information to track or navigate their movement and construct three-dimensional (3-D) models of the chamber. System 14 may be integrated with haptic feedback system 900 as discussed below.

Referring to FIGS. 1-5e, robotic catheter manipulator assembly 300 for operating robotic catheter device cartridges 400, various embodiments of which are described in detail in the aforementioned commonly owned and copending applications, will be described briefly for facilitating an understanding of input control system 100, and the operational integration of haptic feedback system 900 with manipulator assembly 300 for controlling cartridges 400.

Figure 3A:
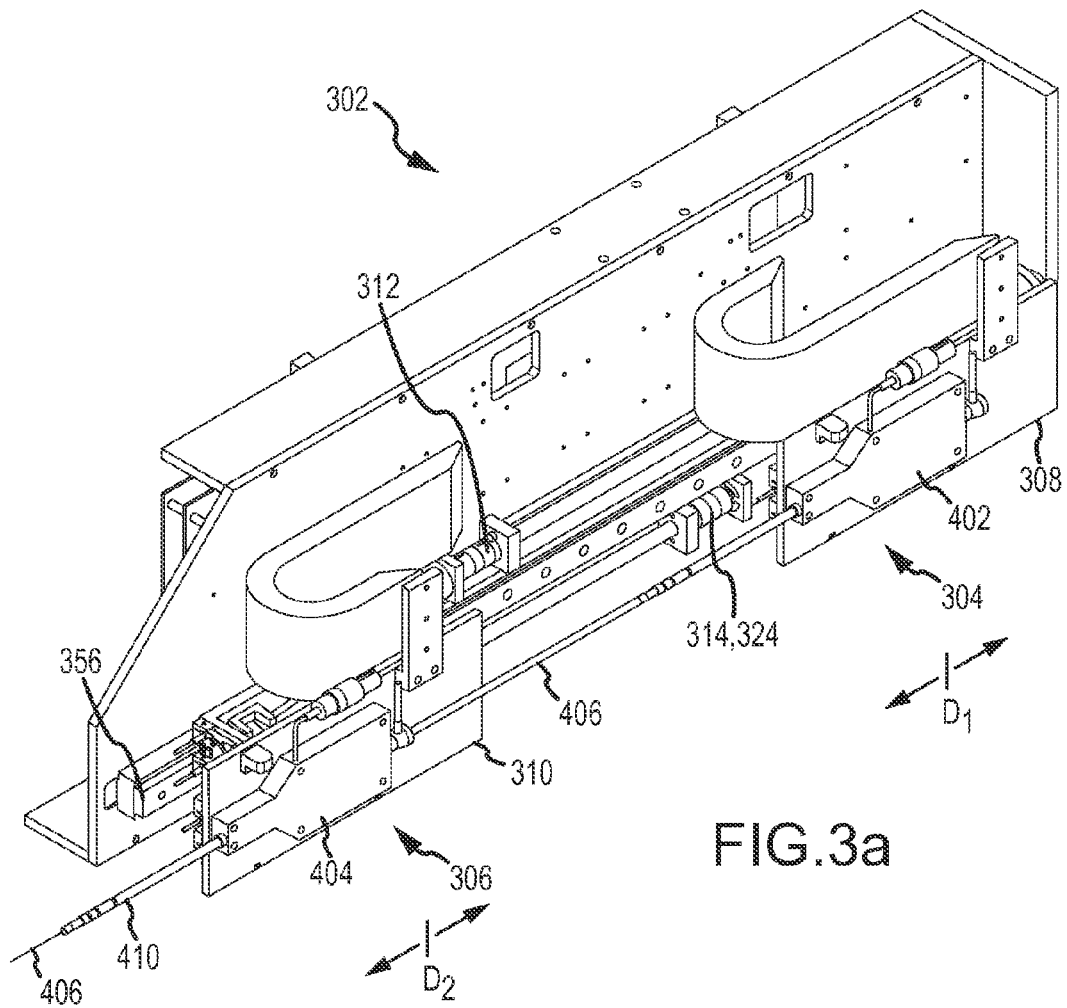
FIGS. 3*a*-3*c* are enlarged isometric views of an embodiment of a robotic catheter manipulator assembly.
Figure 3B:
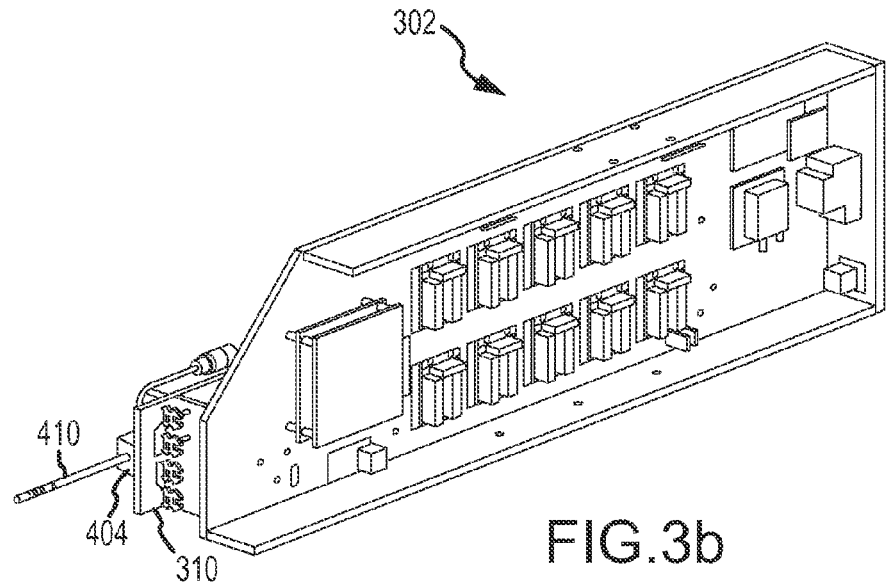
Figure 3C:
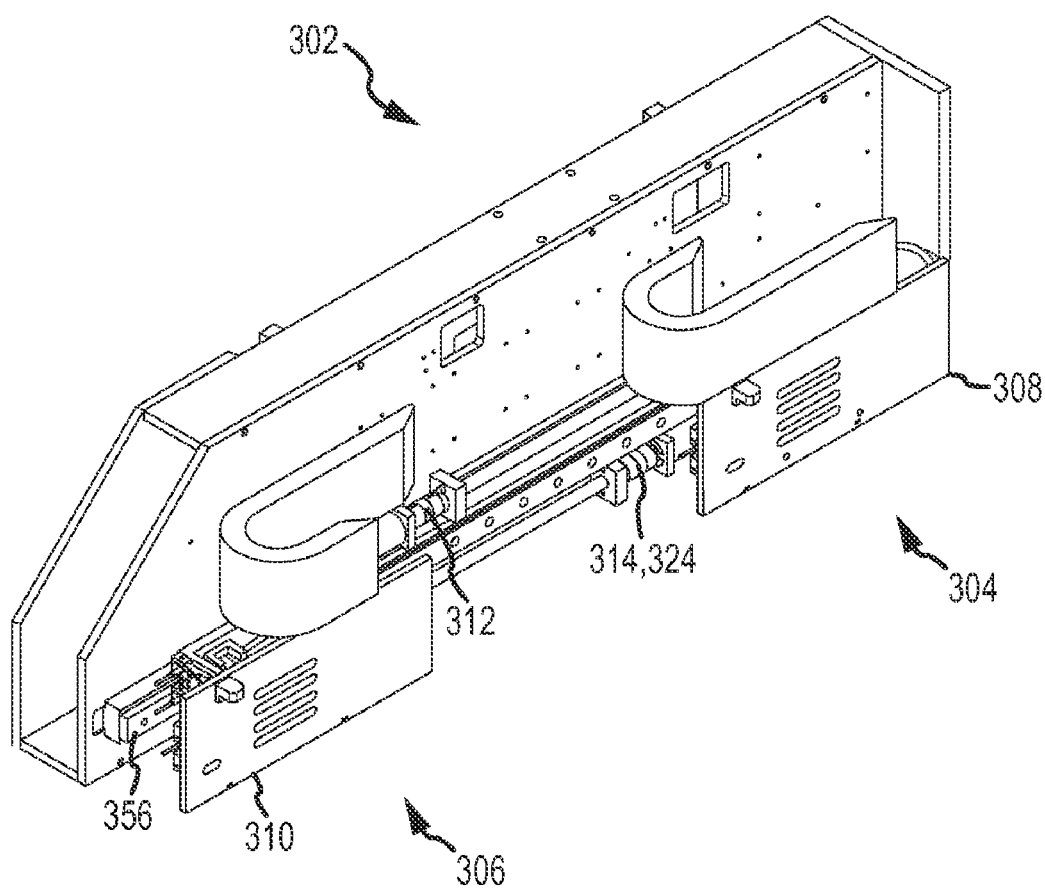
Figure 3E:
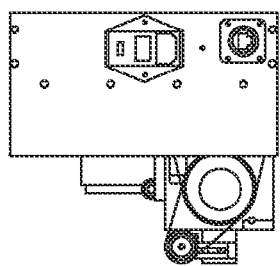
FIGS. 3*d*-3*g* are respectively enlarged left side, right side, top and front views of the robotic catheter manipulator assembly of FIG. 3*a*, illustrating use of the manipulator assembly with a robotic catheter rotatable device cartridge.
Figure 3F:
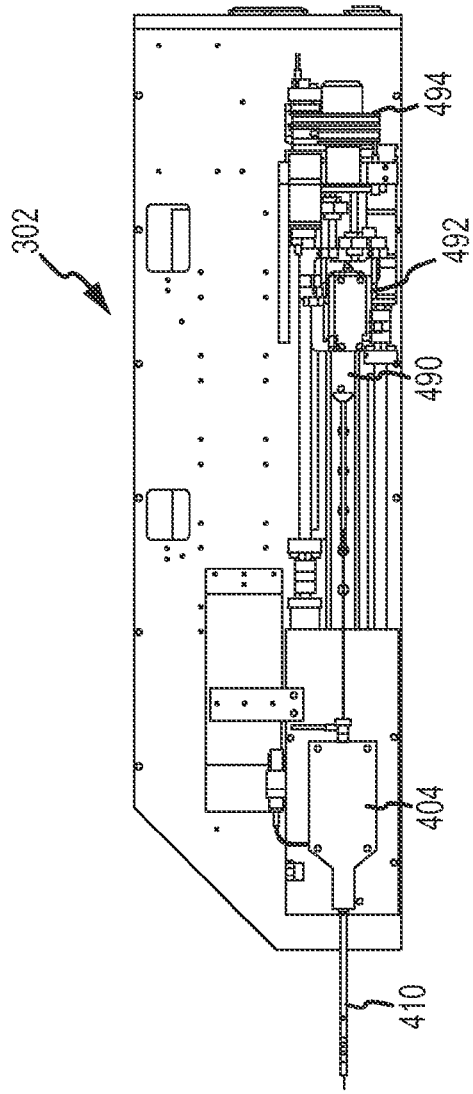
Figure 3D:
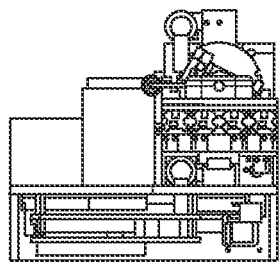

As generally shown in FIGS. 1 and 3a-5e, robotic catheter system 10 which includes one or more robotic catheter manipulator assemblies 300, includes an embodiment of robotic catheter manipulator assembly 302 including both catheter and sheath manipulation mechanisms 304, 306 for manipulating, for example, catheter and sheath cartridges 402, 404. Manipulator assembly 302 may include interconnected/interlocking manipulation bases 308, 310 for catheter and sheath cartridges 402, 404, and likewise may include electrical "handshake" functionality as discussed below. Each interlocking base 308, 310 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 3a, each interlocking base may be translated by high precision drive mechanisms 312, 314. Such drive mechanisms may include, for example and without limitation, a motor driven lead screw or ball screw.

As shown in FIGS. 3a-5e, for each cartridge 402, 404, an associated manipulation base 308, 310 may include a plurality of fingers 316, 318, 320 and 322, (e.g., one per steering wire) that extend or protrude upwardly to contact and interact with the steering wire slider blocks (such as slider blocks 412, 414, 416, 418) to independently tension select steering wires 420, 422, 424, 426. Each finger can be configured to be independently actuated by a precision drive mechanism, such as a motor driven ball screw 324, and may be outfitted with force sensors to measure corresponding steering wire tension. A distal steering wire encoder (not shown) may also be provided for force measurements at the distal end of the steering wires adjacent the catheter distal end. Haptic feedback system 900 may be operatively integrated with the precision drive mechanisms and other components (e.g. fingers, slider blocks, cartridges, manipulation bases, force sensors etc.) of catheter manipulator assembly 302 for providing haptic feedback based on, for example, the movement of steering wires 420, 422, 424, 426, or the orientation and location of assembly 302 and its various components. Each motor driven ball screw (for both finger control and cartridge translation control) may further include encoders to measure a relative and/or an absolute position of each element of the system. As shown in FIG. 4a, bearing 332 and coupler 330 of ball screw 324 may engage frame 340 of respective bases 308, 310 and a corresponding finger 316, 318, 320 or 322 may be mounted adjacent a strain gauge for measuring the corresponding steering wire tension.

Figure 4A:
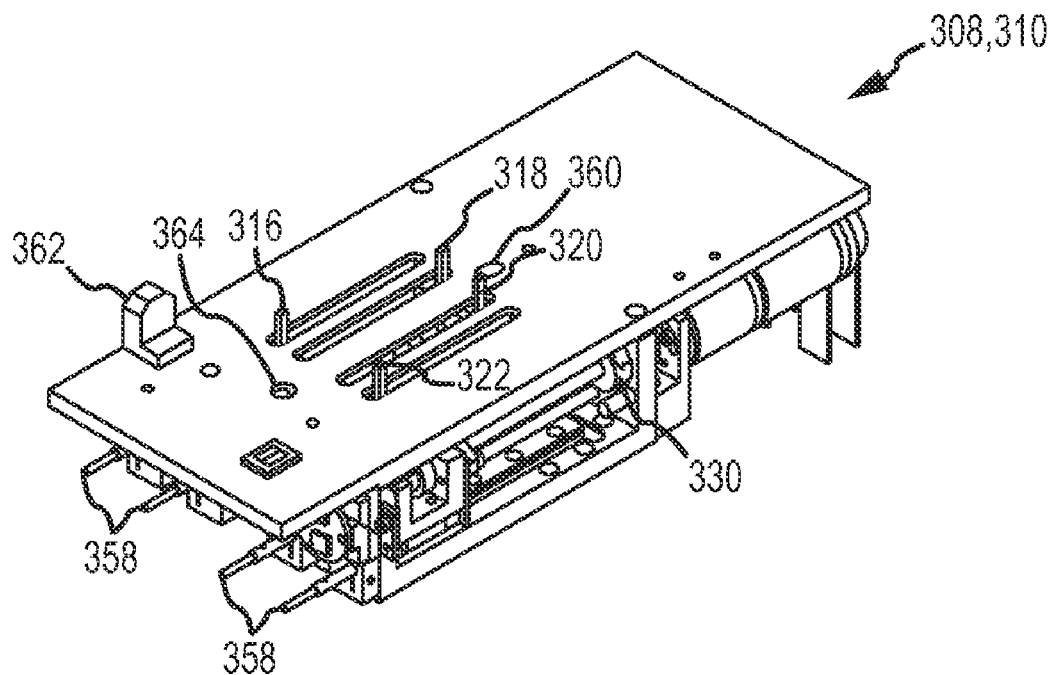
FIGS. 4*a*-4*c* are enlarged isometric views of an embodiment of a manipulation base.
Figure 4B:
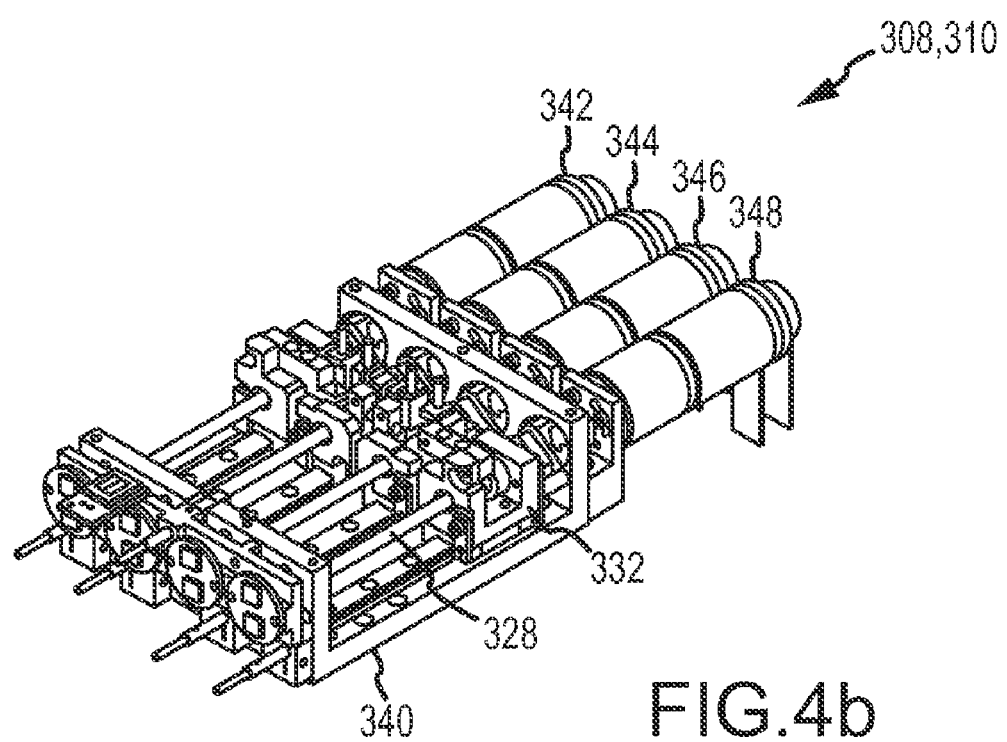
Figure 4C:
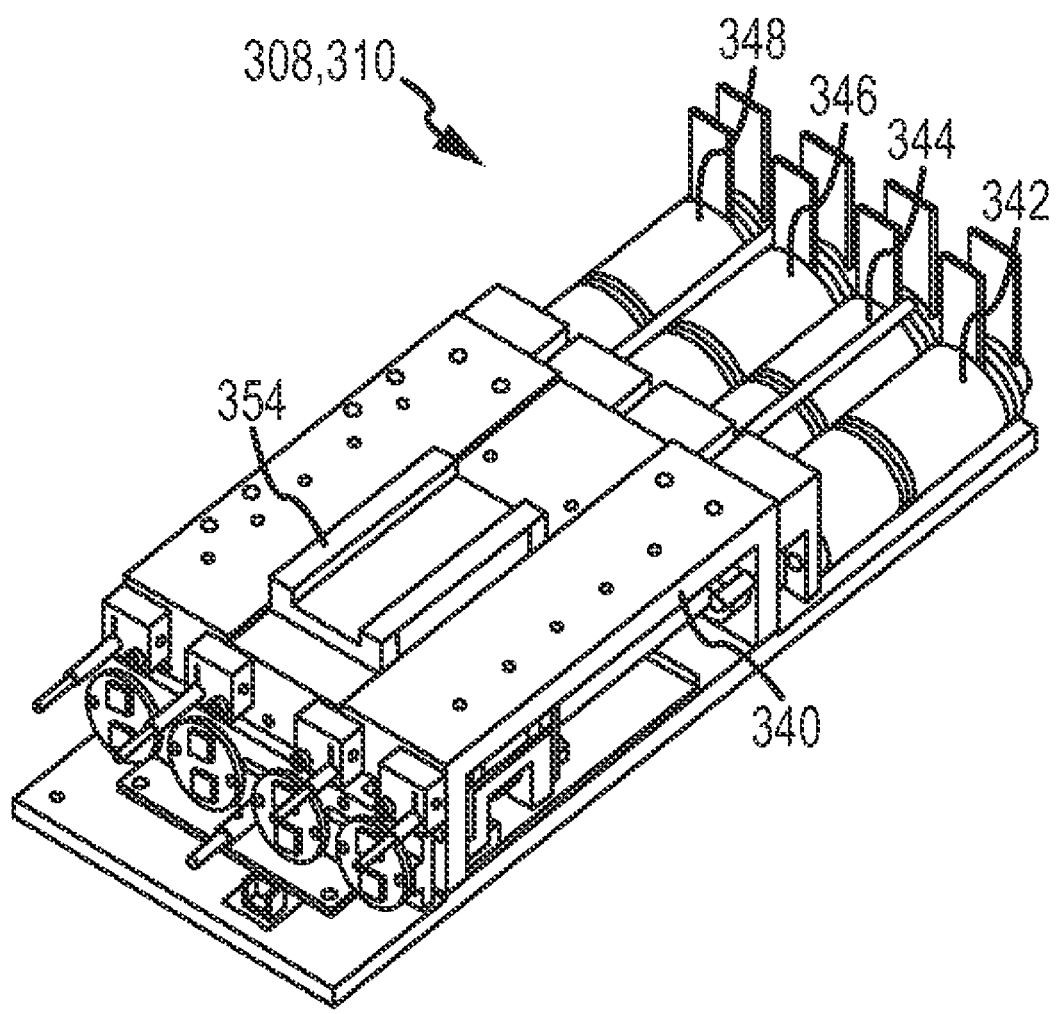

Referring to FIGS. 4a-4c, bases 308, 310 may include exemplary components such as motors 342, 344, 346 and 348, respectively coupled to fingers 316, 318, 320 and 322. A bearing 354 may be provided for sliding of bases 308, 310 on track 356. A plurality of inductive sensors (e.g. home sensors) 358 may be provided for guiding each manipulation base to a safe position. Haptic feedback system 900 may be operatively connected with sensors 358 for providing haptic feedback based on the movement and location of each manipulation base.

Figure 3G:
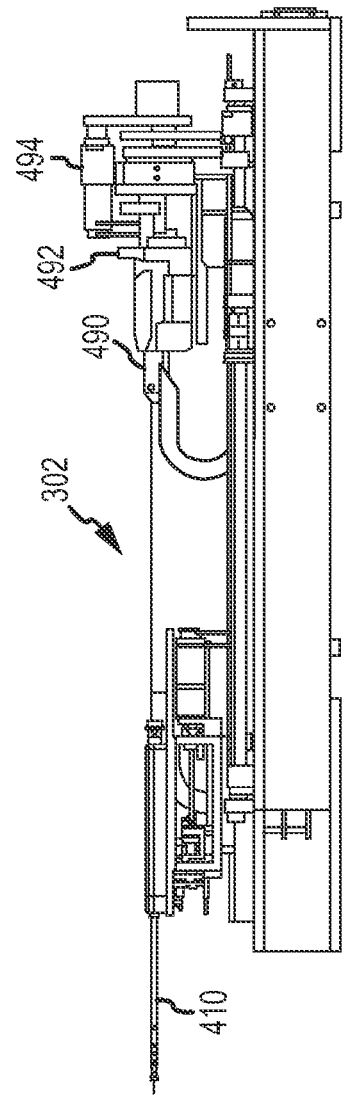

Referring to FIGS. 1-3g, particularly FIGS. 3d-3g, robotic catheter manipulator assembly 302 may be usable with a robotic catheter rotatable device cartridge 490, described in detail in commonly owned and copending application titled "Robotic Catheter Rotatable Device Cartridge." As shown in FIG. 3g, manipulator base 308 may be replaced with a robotic catheter rotatable drive head 492 and a robotic catheter rotatable drive mechanism 494, described in detail in commonly owned and copending application titled "Robotic Catheter Rotatable Drive Mechanism."

Referring to FIGS. 1 and 5a-5e, an embodiment of catheter and sheath cartridges 402, 404 will be described in detail.

As briefly discussed above, robotic catheter system 10 may include one or more cartridges 400, with manipulator 302 including at least two cartridges 402, 404, each of which may be respectively designed to control the distal movement of either the catheter or the sheath. With respect to catheter cartridge 402, catheter 406 may be substantially connected or affixed to cartridge 402, so that advancement of cartridge 402 correspondingly advances catheter 406, and retraction of the cartridge retracts the catheter. As further shown in FIGS. 5a-5e and discussed above, in an embodiment, each cartridge 402, 404 may include slider blocks (e.g., 412, 414, 416, 418), each rigidly (and independently) connected or affixed to one of a plurality of catheter steering wires (e.g., 420, 422, 424, 426) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Haptic feedback system 900 may be operatively connected with the handshake device for providing haptic feedback based on the particulars of a cartridge (e.g., by type and/or proper placement/positioning). Sheath cartridge 404 may be designed in a similar manner as the catheter cartridge 402, but will typically be configured to provide for the passage of catheter 406. Assembly 302 may include a plurality (e.g., as many as ten or more) of independent driving mechanisms (e.g. motor driven ball screws 324).

For some embodiments, the catheter and sheath cartridge can be designed to be substantially similar, and in that context a reference to either may relate to both. For example, as shown in FIGS. 5a-5e, the design of the catheter/sheath cartridge may include upper and lower cartridge sections 428, 430, and independent slider blocks 412, 414, 416, 418. The system is not generally limited to specific material selection or formation techniques. However, in an embodiment, the upper and lower cartridge sections 428, 430 may be injection molded using a polycarbonate material. Each slider block 412, 414, 416, 418 may be connected to a separate catheter steering wire 420, 422, 424, 426, and may be formed of a Teflon-like material such as, for example, Delrin AF. When in contact with the cartridge housing portions 428, 430, such Teflon-like slider blocks may maintain a low static and dynamic coefficient of friction and may avoid the need for additional lubrication.

Figure 5A:
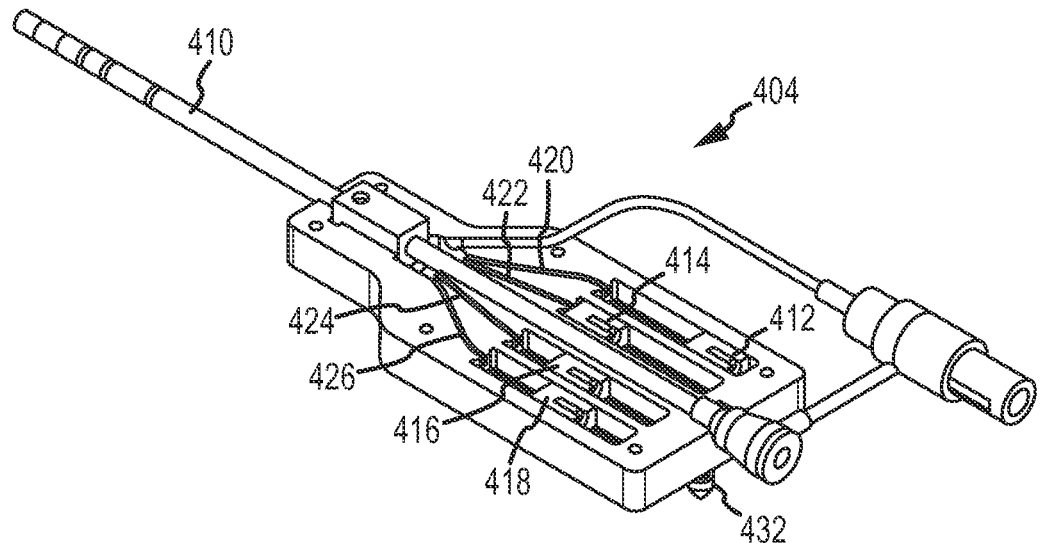
FIGS. 5*a*-5*e* are enlarged isometric views of an embodiment of a robotic catheter device cartridge, with FIG. 3*a* illustrating an exemplary usage of the robotic catheter device cartridge.
Figure 5B:
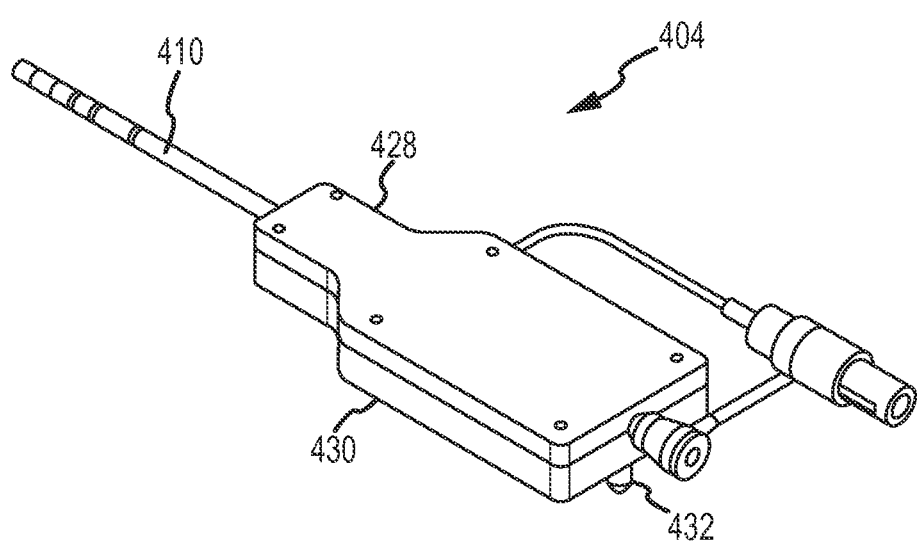
Figure 5C:
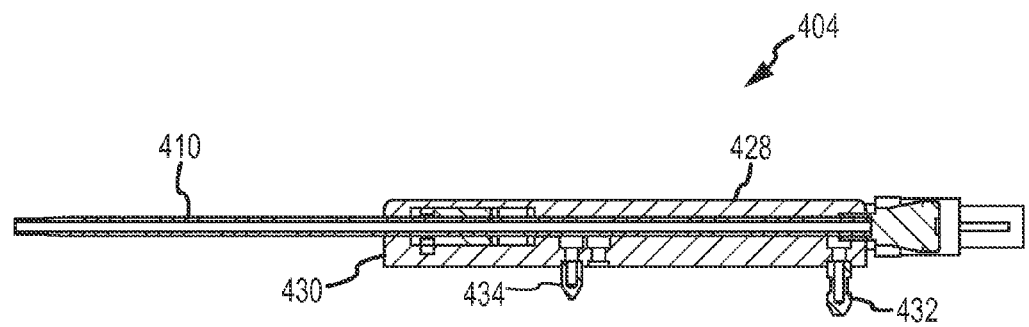
Figure 5D:
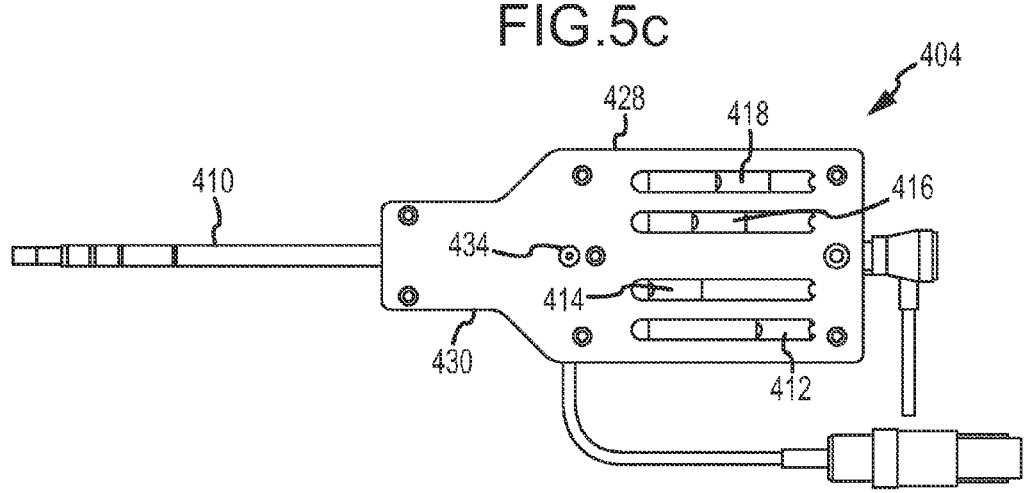
Figure 5E:
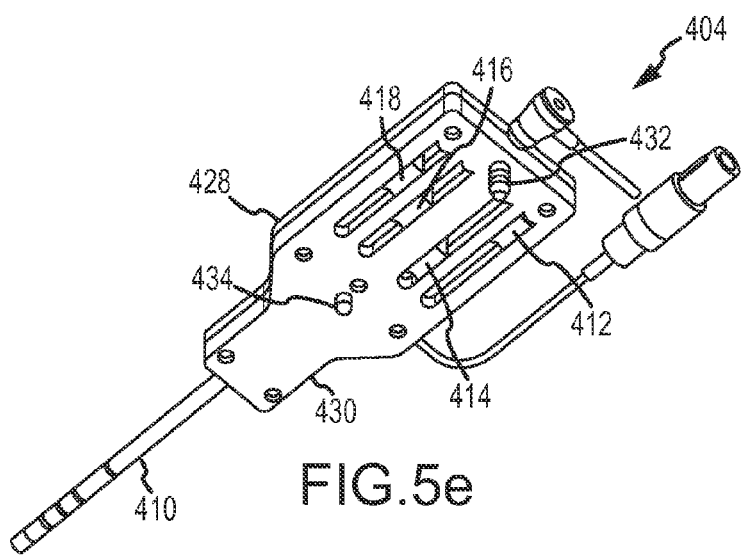

Referring to FIGS. 3a-5e and as discussed above, catheter and sheath cartridges 402, 404 may be configured to secure or lock down onto respective interconnecting catheter and sheath manipulation bases 308, 310. To couple cartridge 402 (and 404) with base 308 (and 310), one or more locking pins (e.g., 432 in FIGS. 5a, 5d and 5e) on the cartridge may engage one or more mating recesses 360 in the base (see FIG. 4a). In an embodiment, such recesses 360 may include an interference lock such as a spring detent or other locking means. In an embodiment, such other locking means may include a physical interference that may require affirmative/positive action by the user to release the cartridge. Such action may include or require actuation of a release lever 362. Additionally, as shown in FIGS. 5c, 5d and 5e, cartridge 402 (and 404) may include one or more locator pins 434 that are configured to passively fit into mating holes on the base (e.g., 364 in FIG. 4a). Haptic feedback system 900 may be operatively connected with various sensors on manipulator assembly 302 for providing haptic feedback based on the attachment/detachment of each cartridge with its respective manipulation base (e.g. during engagement of locking/locator pins 432, 434, and actuation of release lever 362).

In an embodiment, a user (e.g. an EP) may first manually position catheter 406 and sheath 410 (with catheter 406 inserted in sheath 410) within the vasculature of a patient. Once the devices are roughly positioned in relation to the heart, the user may then engage or connect (e.g., "snap-in") the catheter cartridge into place on interconnecting/interlocking bases 308, 310 of manipulator assembly 302, for example, by inserting the locking/locating pins 432, 434 of the cartridges into mating holes 360, 364 of respective base 308, 310. When the cartridge is interconnected with the base, each of the plurality of fingers 316, 318, 320 or 322 may fit into recesses formed between the distal edge of slider blocks 412, 414, 416, 418 and a lower portion of the cartridge housing. Such recesses are shown in, for example, FIGS. 5d and 5e. With sufficiently rigid coupling between each slider block and a corresponding steering wire, pushing a slider block in a proximal direction may cause an attached steering wire to tension and thus laterally deflect the distal end of the catheter and sheath 406, 410. As discussed herein, haptic feedback system 900 may assist a user and provide feedback during attachment, use and detachment of the cartridges.

The aforementioned electrical handshake between manipulation bases 308, 310 and catheter and sheath cartridges 402, 404 will be described briefly.

Robotic catheter system 10 may be useful for a variety of procedures and in connection with a variety of tools and/or catheters. Such tools and/or catheters may include, without limitation, spiral catheters, ablation catheters, mapping catheters, balloon catheters, needle/dilator tools, cutting tools, cauterizing tools, and/or gripping tools. The system may additionally include a means of identifying the nature and/or type of catheter/tool cartridge that is installed for use, and/or position or connection related information. The system may automatically access/obtain additional information about the cartridge, such as, without limitation, its creation date, serial number, sterilization date, prior uses, etc. Haptic feedback system 900 may provide feedback based on the aforementioned variables, such as the nature and/or type of catheter/tool cartridge, the position or connection related information, and additional exemplary variables such as the cartridge sterilization date, prior uses etc., as discussed above. Additionally, haptic feedback system 900 may enable a user to automatically select the haptic type, mode and/or proportionality based on the type of cartridge as detected via the automatic handshake functionality described herein.

Further, some embodiments of the system may include an ability to "read" or detect the type or nature of the connected cartridge through the use of memory included with the disposable cartridge together with some data/signal transmission means. By way of example, each cartridge may contain a chip (e.g., an EEPROM chip) that can be electrically interfaced by the manipulator head. Such a chip could, for instance, be programmed during the manufacturing process and may electronically store various data, such as the make; model; serial number; creation date; and/or other special features associated with the cartridge or tool. Additionally the chip may contain other worthwhile information, such as an indication of previous use, catheter specific calibration data, and/or any other information that may relate to the safety or performance of the particular device. Haptic feedback system 900 may be operatively integrated with the aforementioned data/signal transmission means to provide feedback to a user based on the exemplary cartridge particulars discussed above.

In an embodiment, upon interconnecting the cartridge (e.g. 402, 404) with the manipulator head (e.g. 302), a detection means, such as an optical or magnetic sensor, may initially detect the presence of the cartridge. Once presence is detected, the manipulator may energize a chip and initiate data/signal retrieval. Such retrieved data/signal may then be used by the system to control or alter various features and/or displays based on the type of device and/or information provided. While one embodiment may use a chip (e.g., EEPROM), due to its design flexibility, another embodiment may include a wireless transmission device, such as an RFID, which may be employed to facilitate the data storage/transfer instead of, or in addition to a chip. Haptic feedback system 900 may provide feedback based on the aforementioned variables, such as upon attachment of a cartridge and subsequent use thereof.

Referring to FIGS. 1 and 6a-10, haptic feedback system 900 for input control system 100 discussed herein and in further detail in commonly owned and copending applications titled "Robotic Catheter System Input Device" and "Robotic Catheter System with Dynamic Response," will be described in detail.

Figure 6A:
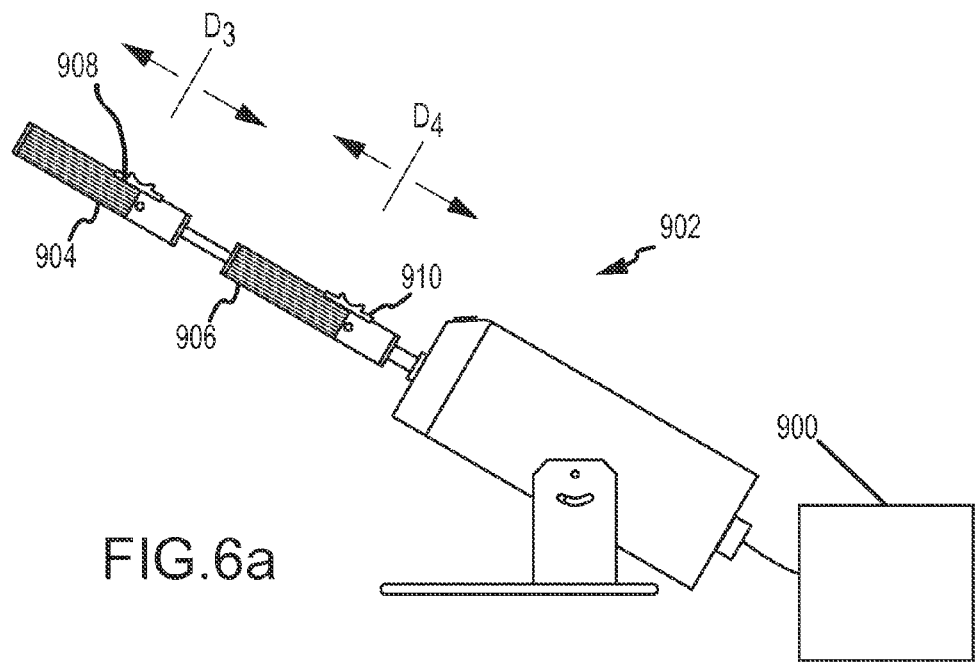
FIGS. 6*a* and 6*b* are exemplary isometric views of a user-interface device in the form of a joystick usable with the robotic catheter system of FIG. 1, operatively connected to the haptic feedback system of FIG. 1.
Figure 6B:
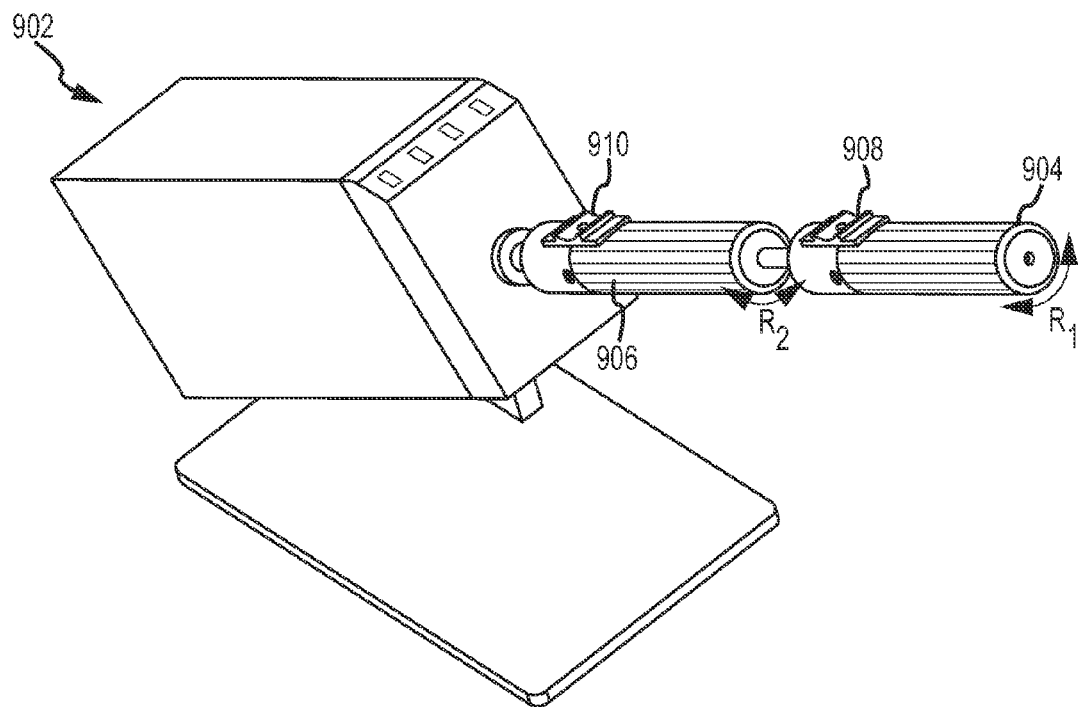

Specifically, an embodiment of robotic catheter system 10 including haptic feedback system 900 may include or be operationally connected to a user interface device 902 (see FIGS. 1 and 6a). For some embodiments such a device may be analogous to a joystick—allowing a user to provide input to the system in a manner mimicking traditional catheter handle controls. As generally shown in FIGS. 6a and 6b, an embodiment of the system may provide instrumented sheath and catheter handles 904, 906 (or vice-versa), respectively, that are able to longitudinally translate (e.g., in directions $D_3$ and $D_4$), independently rotate (in directions $R_1$ and $R_2$), and/or include one or more movable thumb tabs (e.g., elements 908, 910). To record the user's input, each degree of movement may be instrumented, for example, with a potentiometer or motor/encoder. Haptic feedback system 900 may be operationally connected to the potentiometer or motor/encoder to provide feedback during manipulation of user interface device 902.

Mimicking traditional, manual catheter control, an embodiment of robotic catheter system 10 including haptic feedback system 900 may be configured such that longitudinally translating the input handle may cause a respective longitudinal translation of the catheter/sheath distal tip. However, unlike the traditional, manual catheter, the automated catheter system would generally effectuate this translation by advancing or retracting the cartridge. Further, robotic catheter system 10 can be configured so that the rotation of either handle causes a virtual rotation of the catheter/sheath tip, and movement of a thumb tab causes a deflection in the current deflection plane. Haptic feedback system 900 may be configured to provide virtual and/or augmented feedback, as discussed below, during such movement or rotation of the catheter.

In an embodiment of user interface device 902, any or all motion controls of the device can be associated with/employ a spring or servo motor centering feature that returns each control element to a set or "home" location after the element is released. Such a centering feature can allow for highly precise movement corrections of the distal tip by registering various input movements as incremental movements from the "home" location rather than by registering movement entirely in absolute terms.

In an embodiment, instead of thumb tab-type controls, user interface device 902 may additionally include or substitute displacement dial controls. Furthermore, to suit the desires of the user, an embodiment of such a user interface device may permit the handles to be fully interchangeable so that various combinations of controls (e.g., dial and thumb tab handles) can be used for catheter/sheath input. In another embodiment, user interface device 902 may further include safety buttons (e.g. "dead-man switches") that must be pressed for any joystick movement to be registered by the system. This design would prevent inadvertent motion from affecting the position of the actual catheter tip. In yet another embodiment, user interface device 902 may further include a virtual reality surgical system, wherein the physician could be positioned within a cardiac environment (see FIG. 1), and physically position the catheter where desired or needed. As discussed below, haptic feedback system 900 may be integrated with the virtual reality surgical system to guide a user during movement and operation of a catheter.

Figure 7A:
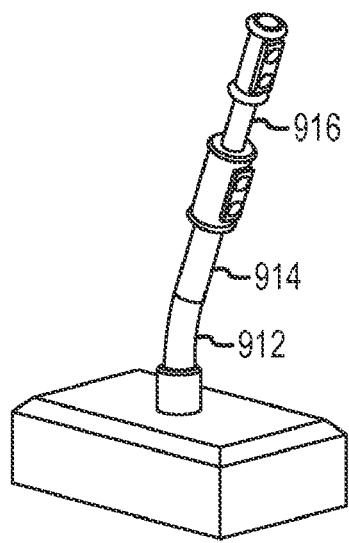
FIGS. 7*a*-7*e* are views of an exemplary construction of the joystick of FIGS. 6*a* and 6*b*.
Figure 7B:
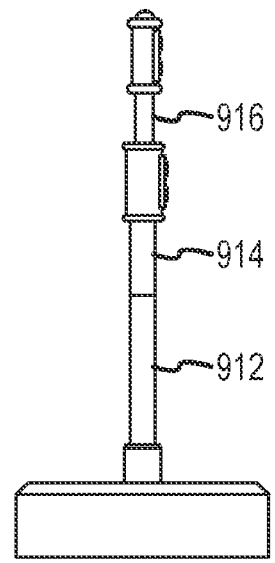
Figure 7C:
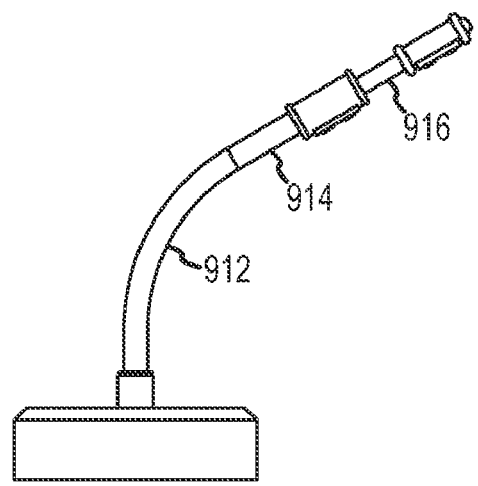
Figure 7D:
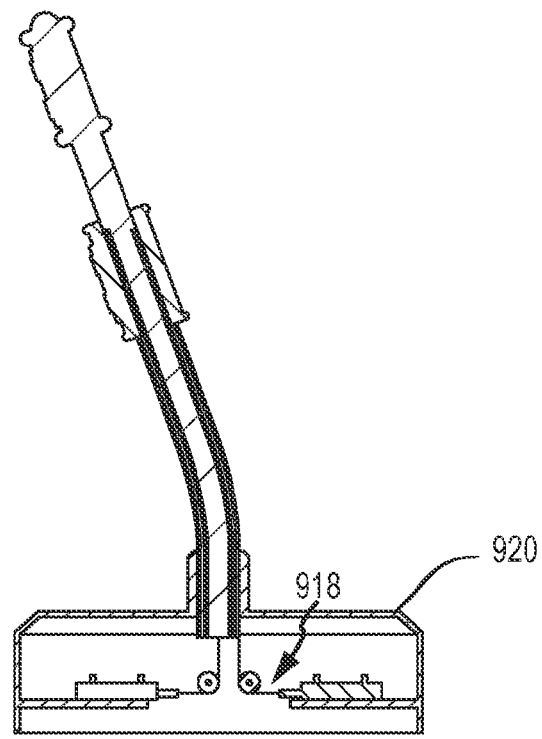
Figure 7E:
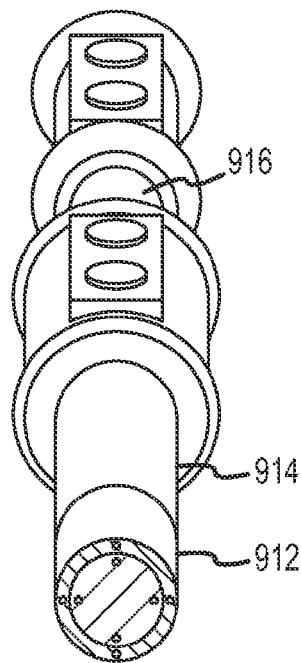

As generally shown in FIGS. 7a-7e, the physical construction of such a device for user interface device 902 may be similar to that of an actual catheter, though on a different scale. As shown in FIGS. 7d and 7e, by way of example, the various sections may be constructed with pull wires, wire ducts, and variable stiffness sections 912, 914, 916 associated with a conventional catheter. In an embodiment, all motions of this device may be configured with a centering feature (e.g., a spring centering mechanism 918), wherein the device inherently returns to an initial position when released. This configuration may be useful or suitable for an incremental input control scheme. Motors, heaters, coolers and other such devices, provided in feedback sub-system 920, may be operationally connected to user interface device 902 for providing the mechanical or thermal feedback via haptic feedback system 900.

In other embodiments, the device may be constructed without a centering mechanism, where the absolute position of the device might instead be used to control the absolute position of the actual sheath and catheter. With such an absolute approach, the input device's physical limitations may be designed to mimic an actual catheter's and sheath's physical limitations (e.g., movement restrictions based on bend radius, catheter retracted into sheath, etc.). Haptic feedback system 900 may be configured to provide feedback during such positioning of user interface device 902.

To record user input, each degree of movement can generally be instrumented with either a potentiometer or motor/encoder. If a motor/encoder is used, haptic feedback system 900 may provide feedback, for example, if the catheter were to contact a virtual wall. An embodiment of this invention may also include an ablation activation button on the distal end of the device.

Referring to FIGS. 1 and 6a-10, when user interface device 902 controls a catheter (see for example catheter 406 of FIG. 3a), amongst other features discussed below, a user, such as an EP, may sense when catheter 406 contacts a tissue during use. Exemplary catheter systems for detecting such tissue contact are disclosed, for example, in commonly owned and copending applications titled "System and Method for Measuring Force and Torque Applied to a Catheter Electrode Tip," "Optic-Based Contact Sensing Assembly and System," and "Accelerometer-Based Contact Sensing Assembly and System," the respective disclosures of which are incorporated herein by reference.

Specifically, during manipulation of a catheter, haptic feedback system 900 may provide mechanical resistance or feedback to a user via user interface device 902 so that the user can sense or feel a response provided by device 902, thus giving the user the perception of actual manipulation of a catheter, similar to manual manipulation of a catheter. Exemplary forms of mechanical resistance may include passive resistance, active push/pull, vibration, etc. In the case of passive resistance or active pushing/pulling, movement of user interface device 902 may be dampened or otherwise restricted when a catheter approaches various speed zones, as discussed below with reference to FIG. 10. In the case of vibrations, as discussed herein, user interface device 902 may be vibrated as a user approaches an endocardial wall, as sensed by the contact/proximity sensors described in the aforementioned copending applications. Feedback may also be from measured applied forces, such as the strain sensors that monitor the pull wires or manipulation bases, with such feedback being useful, for example, for transseptal applications.

An embodiment of user interface device 902 may include touch-type feedback via haptic feedback system 900 which may involve forces generated by a motor (e.g. disposed in feedback sub-system 920 of FIG. 7*d*) connected to user interface device 902 that the user can feel while holding the device. These forces may be based on actual or computed forces being applied to a physical catheter tip. In an embodiment, the unit may sense forces using a force and/or impedance sensor in the tip of the catheter and generate a corresponding force on sheath and/or catheter handles 904, 906 (see FIG. 6*a*). In other embodiments, the forces can be based on a computed geometric model of the cardiac anatomy, such as that associated with the St. Jude Medical, Inc. EnSite™ system (see discussion below).

In an embodiment, haptic feedback may be conveyed to a user by employing an input device instrumented with motors/encoders on each degree of freedom. Though the motors may operate in a passive mode for a majority of the procedure, if feedback is required by the system, the motors may be energized to produce a torque on sheath and/or catheter handles 904, 906 capable of retarding the user's movement in particular degrees of freedom. While in a passive mode, the motor typically will not produce a significant retarding force, however the attached encoder may record the input for use in visualization and control routines.

Prior to a haptic response being conveyed, haptic feedback system 900 may first calculate the appropriateness and magnitude of such a force. In an embodiment, such a force may attempt to replicate a contact between an actual catheter tip and a portion of the cardiac anatomy. In an embodiment, as discussed above, such contact may be either directly sensed through one or more force sensors on the distal tip of the catheter/sheath, or may be calculated based on a virtual catheter/sheath position within a rendered geometric computer model.

In an embodiment where haptic forces are based on actual catheter contact, as discussed above, the catheter's distal tip may be instrumented with a force sensor. Such a force sensor may include, without limitation, load cells, shape memory alloy based force sensors, piezoelectric force sensors, strain gauges, or optical-based or acoustic-based force sensors. In other embodiments, a contact sensor may be based on electrical contact, such as those associated with detected impedance.

In an embodiment employing actual contact sensing, the sensor may generate a signal representative of the actual physical or electrical contact. Based on the magnitude and direction of the force, as well as the current position of the input device, haptic feedback system 900 may produce a corresponding torque on the input device (e.g. user interface 902 or 930) that may resist further movement through the obstructing anatomy. The system can be configured so that the user would feel this reaction force as if the input device was impacting a virtual wall.

Based on the system calibration, the resistive force the user feels at the input joystick could be more or less "spongy." That is, haptic feedback system 900 could be tuned so that a tip impact with the cardiac wall is either felt like a rigid impact with an immovable object, or perhaps as a contact with a soft sponge.

Haptic feedback (e.g. vibration, force, temperature etc.) may also be proportional to predicted risk, such as cardiac wall thickness, prior surgical knowledge, and other anatomical information. For example, resistance approaching the wall of the left ventricle may be less than that approaching the atrial appendage.

Haptic feedback based on virtual catheter tip proximity to virtual cardiac anatomy will now be discussed in further detail.

As briefly discussed above, haptic feedback system 900 may include virtual and/or augmented reality modes a user may optionally program for user-specific responses. For example, in the virtual reality mode, a user may optionally make selections to experience the aforementioned feedbacks (e.g. passive resistance, active push/pull etc.) via user interface device 902 so that the feedbacks correspond to forces experienced by a user during manual insertion and operation of a typical catheter. In the case of passive resistance, user interface device 902 may be dampened when a catheter electrode tip (not shown) is in the vicinity or in contact with endocardial tissue. Alternatively, in the case of active push/pull, user interface device 902 may be pushed/pulled in an opposite direction to alert a user of potential contact with endocardial tissue. The amount of force feedback may be modulated, such that the amount of force is proportional or scaled/amplified to the signal being provided by a sensor (e.g. a contact sensor). In the case of tissue, the force may be modulated to provide a "soft" feeling, so that a user is aware of contact with tissue.

For a specific example of haptic feedback in the virtual reality mode, in the case of a catheter having a temperature sensor, the handle of user interface device 902 may be heated or cooled as the temperature at a catheter electrode tip (not shown) or contact area heats or cools between predetermined temperature thresholds. The temperature of user interface device 902 may of course be scaled up or down based on specific user requirements and tolerance factors. For example, in the case of a cryocatheter for which the catheter tip temperature reaches liquid nitrogen temperatures, the temperature variation of user interface device 902 may be scaled to safe levels detectable and tolerable by a user.

The virtual feedback, in an embodiment, may be based on lesion quality, and calculated, for example, from time of burn and power input, measured impedance, and/or effects of electrogram.

In an embodiment, haptic feedback forces may be conveyed to a user via exemplary user interface devices 902, 930 based on contact forces computed from the proximity between a virtual catheter model and a computer-generated representation of the cardiac anatomy. In an embodiment, the catheter positioning may be obtained through an impedance-based position detection system (e.g., such as associated with St. Jude Medical's EnSite NavX™ Navigation and Visualization system). Further such a computer-generated representation of the cardiac anatomy may be derived from prior CT or MRI data, or a model (such as that created or maintained by St. Jude Medical's EnSite™ system).

With such embodiments/configurations, a user may have a previously obtained geometric model of the cardiac anatomy. This model may be visible to an EP user through a visualization system (such as St. Jude Medical's EnSite NavX™ Navigation and Visualization system; see also visualization system 12 of FIG. 1). This model may be assembled using, for example, previously captured CT or MRI images, and/or "skinned" geometry obtained by sensing actual position data of a mapping catheter (e.g., with St. Jude Medical's EnSite NavX™ Navigation and Visualization system). Once the model is assembled, a catheter locating system (e.g., St. Jude Medical's EnSite NavX™ Navigation and Visualization system) could then place the working catheter inside the computed geometric model. In an embodiment, as the catheter is moved within the geometry, haptic feedback system 900 may be used to compare the positioning of the catheter to that of the generated geometry. If the catheter is perceived to be in contact with the generated geometry, a resistive force could then be generated in connection with the associated input device—e.g., using attached motors. In this regard, the resistive force could be generated when the catheter is at a predetermined distance from the tissue and increase as the catheter approaches. The resistive forces could increase dramatically when the catheter passes through the model wall to prevent perforation of the endocardial wall.

In an embodiment, the geometric model may be registered to a repeating physiological signal such as, for example, the cardiac rhythm or respiration rhythm. As this signal is sensed in the actual procedure, the model geometry may dynamically change. This may then enable computed haptic feedback to provide a more accurate representation of the contact actually occurring within the patient.

In the aforementioned augmented reality mode, haptic feedback system 900 may be pre-programmed or a user may optionally make selections to experience enhanced feedback in the form of force, or temperature, vibration or other forms of feedback, not necessarily corresponding, for example, to forces experienced by the user during manual catheter operation, such as, pressure, elasticity, angle of attack, texture, oscillations caused by cardiac or respiratory motion, and others. For example, a signal from a temperature sensor on an electrode tip during ablation may be converted to a force or vibration signal to alert a user of, for example, tissue overheating. Texture could be obtained from such information as a high frequency signal on the force sensor while in contact with tissue, medical imaging such as CT or MRI, or apriori knowledge of anatomy imparted into surface models of the endocardium.

Vision recognition from fluoroscopy images, MRI and/or CAT, and/or impedance measurement, may also be used for feedback information. An accelerometer (not shown) attached to an EnSite NavX™ Navigation and Visualization patch (not shown), may be used to monitor and stabilize (e.g. cancel out) the effect of patient respiration, or movement to improve haptic stability.

Integration of haptic feedback system 900 with other subsystems of robotic catheter system 10, such as visualization system 12, EnSite™ system 14 and manipulator assembly 300 will now be described.

For haptic feedback system 900, as discussed above, a variety of other sources, such as St. Jude Medical's EnSite™ system 14, may be integrated with system 900 to provide haptic feedback to a user based on virtual catheter navigation (e.g. visualization system 12 including EnSite NavX™ Navigation and Visualization monitor 16). For example, for the EnSite NavX™ Navigation and Visualization system, a rendering of a catheter may be displayed against the backdrop of a cardiac geometry in 3D, with the location of the catheter being determined by electrical impedance or magnetic localization technology (disclosed in commonly owned and copending application titled "Method and Apparatus for Collection of Cardiac Geometry Based on Optical or Magnetic Tracking." Both of these electrical impedance or magnetic localization systems provide the ability to collect geometry by visiting a multitude of physical locations and simultaneously recording those positions as a "point cloud". A surface can then be fit around the cloud of points. Alternatively both systems offer the ability to import and register pre-acquired geometries derived from sources such as a segmented CT or MRI scan. By observing when the catheter is in the proximity or touching this 3D geometry, haptic feedback system 900 may provide elastic or other forms of resistance to motion that advances a catheter closer to the endocardial wall. This can provide a user with knowledge that they are in contact with the endocardial wall and furthermore restrict their ability to advance the catheter further. Further, such a system can allow a catheter electrode without a contact sensor to be used in the event alternate instrumentation is required on the limited space available on a catheter electrode.

As discussed above, haptic feedback system 900 may be operatively connected to catheter manipulator assembly 300 (and assembly 302) to prevent further motion of catheter and/or sheath cartridges 402, 404, and their respective manipulation bases 308, 310. System 900 may also be operable with assembly 300 to control the speed of movement of catheter and sheath cartridges 402, 404, and their respective manipulation bases 308, 310. The control may include both high precision drive mechanisms 312, 314, motors 342, 344, 346, 348, and any other motorized components of assembly 300, including cut-off for power to such components.

Figure 8:
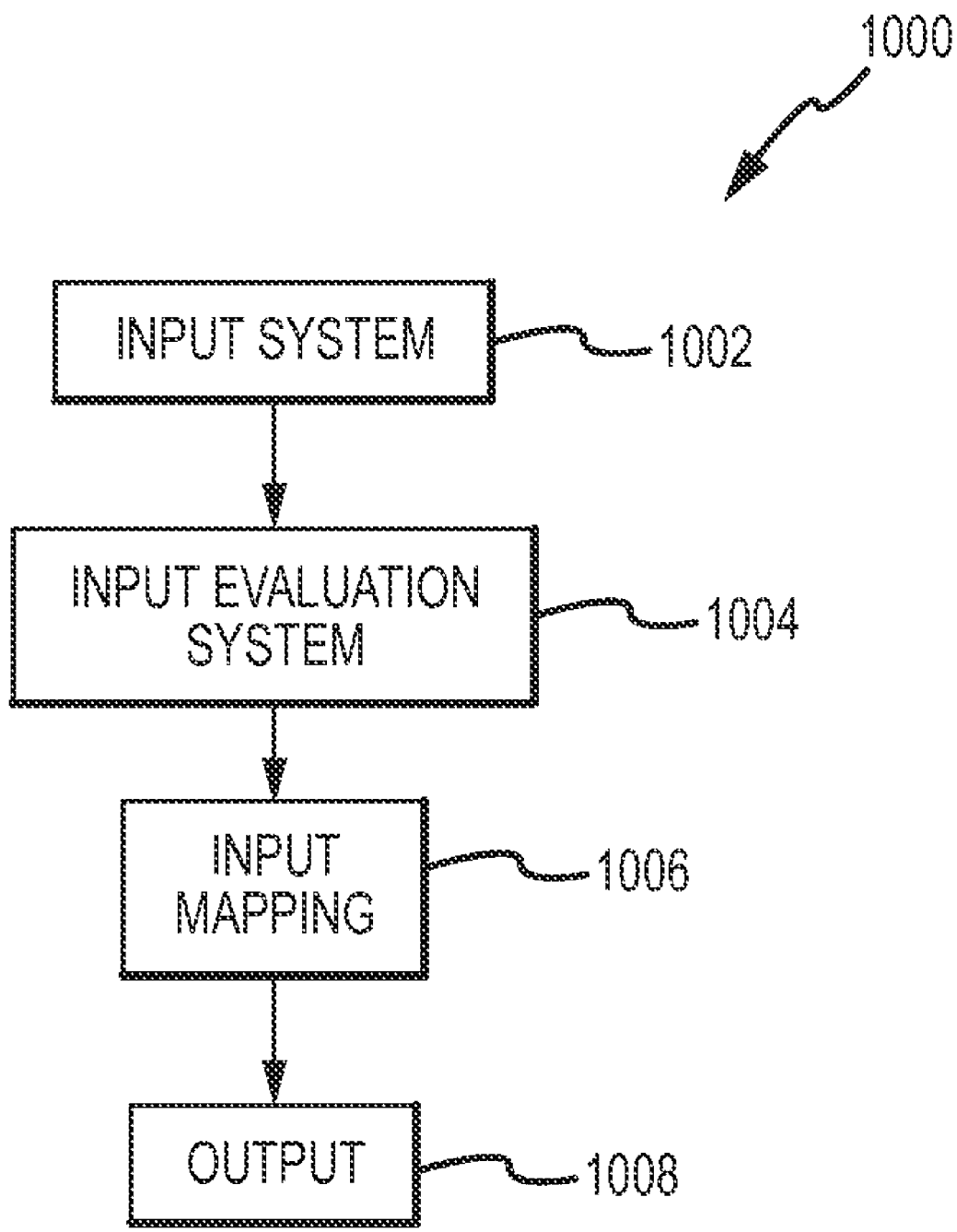
FIG. 8 is a flowchart of an exemplary control system for the haptic feedback system according to the invention.

Referring to FIG. 8, an exemplary control system 1000 for haptic feedback system 900 will now be described.

Referring to FIG. 8, control system 1000 may generally include an input system 1002 for registering input signals from any of a variety of the aforementioned sensors provided with haptic feedback system 900, such as those with catheter manipulator assembly 300 (and assembly 302), catheter and/or sheath cartridges 402, 404, and their respective manipulation bases 308, 310. Input system 1002 may further register input signals from, for example, force and torque sensors provided on an electrode or structure on catheter 406, such as those disclosed in commonly owned and copending applications titled "System and Method for Measuring Force and Torque Applied to a Catheter Electrode Tip," and "Optic-Based Contact Sensing Assembly and System."

The inputs received by input system 1002 may be evaluated at input evaluation system 1004 to determine, for example, the location, magnitude and other relevant variables of a signal. For example, input evaluation system 1004 may evaluate the magnitude of a force or torque applied to a catheter tip, and compare it to predetermined and/or measured values for force or torque for determining a level and/or type of haptic feedback. Alternatively, input evaluation system 1004 may evaluate the magnitude of tension on a steering wire (e.g. steering wires 420, 422, 424, 426), or any of the signals or variables discussed herein. Based on the evaluation performed at input evaluation system 1004, system 1004 may map the results at location 1006 to the exemplary outputs discussed herein (e.g. a signal from a temperature sensor on an electrode tip during ablation being converted to a force or vibration signal to alert a user of, for example, tissue overheating).

With the results being mapped at location 1006, control system 1000 may generate an output at location 1008 to, for example, user interface device 902 to alert the user as discussed herein.

A user interface device 902 in the form of an instrumented glove 930, also operable with haptic feedback system 900, will now be discussed.

Figure 9:
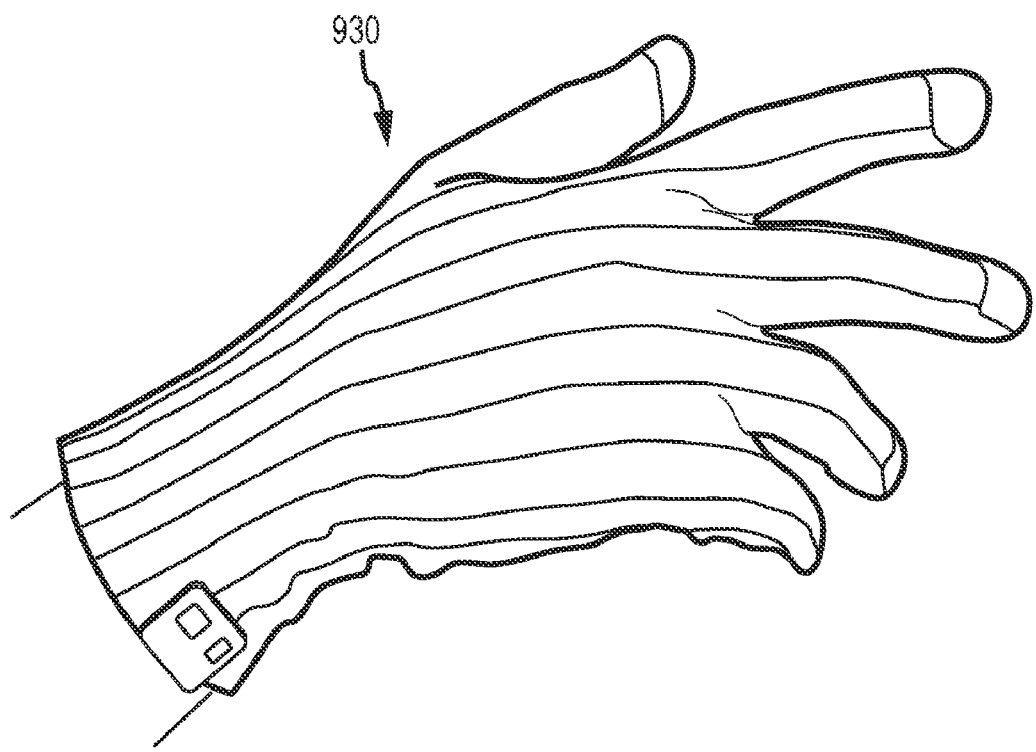
FIG. 9 is an exemplary isometric view of another user-interface device in the form of a glove.

Referring to FIG. 9, for some embodiments of robotic catheter system 10, user interface device 902 may include or take the form of an instrumented glove. In an embodiment, the user's/wearer's index finger may be instrumented to act as a virtual catheter tip, and haptic feedback system 900 may provide feedback at the user's/wearer's index or another finger. In another embodiment, the user may have the ability to manipulate the actual catheter tip by interacting with a virtual representation of the tip. For such a user interface device, the user may wear a glove, similar to glove 930, instrumented with sensors (such as accelerometers and position sensors). This device may then manipulate or interact with a 3-dimensional visualization of the catheter and/or heart anatomy, for instance, through holographic imagery.

In an embodiment of such an input control means, a remote control "glove-type" system may be further implemented within a liquid tank (e.g., water tank), where field generators (such as those associated with the EnSite NavX™ Navigation and Visualization system marketed by St. Jude Medical) are externally attached. For such embodiments, an instrumented glove may extend into the tank while a user's finger (e.g., index finger) or other portions of the glove are instrumented with electrodes to enable detection of position and orientation information for the entire glove or portions of the glove. Haptic feedback system 900 may likewise provide feedback at the user's/wearer's index or another finger, in a similar manner as instrumented glove 930.

In an embodiment, electrodes (e.g., EnSite NavX™-type electrodes) may be positioned on a user's index finger to correspond with similar electrodes on the catheter, where a movement of the glove electrodes can be configured to cause a corresponding movement of the actual catheter electrodes. Haptic feedback system 900 may be integrated with such electrodes to provide scaled feedback. Further, if desired, an incremental movement control scheme may be implemented by incorporating an activation switch, such as, for example, a foot pedal. Such a control/switch may indicate to the system that successive movements should be recorded for later use (e.g., for the purpose of control).

Orientation vector display in visualization software to show direction of thumb switch deflection (e.g. thumb switches 908, 910 of FIG. 6*a*) will now be discussed.

With some traditional, non-robotic catheter procedures, a thumb switch on the catheter handle causes catheter deflection by tensioning a corresponding steering wire. Such a switch typically allows the distal tip of a catheter to laterally deflect in one of two opposing directions in a single plane. If deflection is desired in more than one plane, a user commonly must physically rotate the catheter about its longitudinal axis to cause the deflection plane to rotate.

Unlike traditional non-robotic controls, robotic catheter system 10 does not require physical rotation of the catheter to achieve a similar positioning result. The system instead can achieve 360-degree movement of the distal tip through the use of four (or more) steering wires (except when using a rotatable cartridge as illustrated in FIGS. 3*d*-3*g* and discussed in commonly owned and copending application titled "Robotic Catheter Rotatable Device Cartridge"). In an embodiment, each of four steering wires is equally spaced around the catheter's/sheath's circumference (e.g., positioned 90 degrees apart). In an embodiment incorporating instrumented traditional catheter handle input controls, as described above, an indicator may be provided to give the user an idea of which direction the distal tip will deflect if the thumb switch is actuated. Such an indicator may be operatively connected with haptic feedback system 900 to signal to a user (e.g. by pulse direction or number of pulses) the direction of movement of the distal tip.

An embodiment of robotic catheter system 10 provides an indication of the deflection direction by including a representation (e.g., a deflection plane vector) on a computer visualization (e.g., a display such as provided in connection with St. Jude Medical's EnSite™ system). In an embodiment, such a representation (e.g., vector) may include an arrow superimposed near the tip of the virtual representation of a physical catheter. Such an arrow may indicate the direction the catheter would move if the thumb switch were pulled toward the user. Similarly, pushing a control (e.g., thumb switch) may cause the catheter to deflect in the opposite, arrow tail direction. The user may then cause a rotation of this vector by rotating an input handle, which may then be sensed by the attached motor/encoder or potentiometer. Similarly, a deflection vector could be associated with sheath visualization. Such vectors may be operatively associated with haptic feedback system 900 to signal to a user (e.g. by pulse direction or number of pulses) the deflection direction(s).

Figure 10:
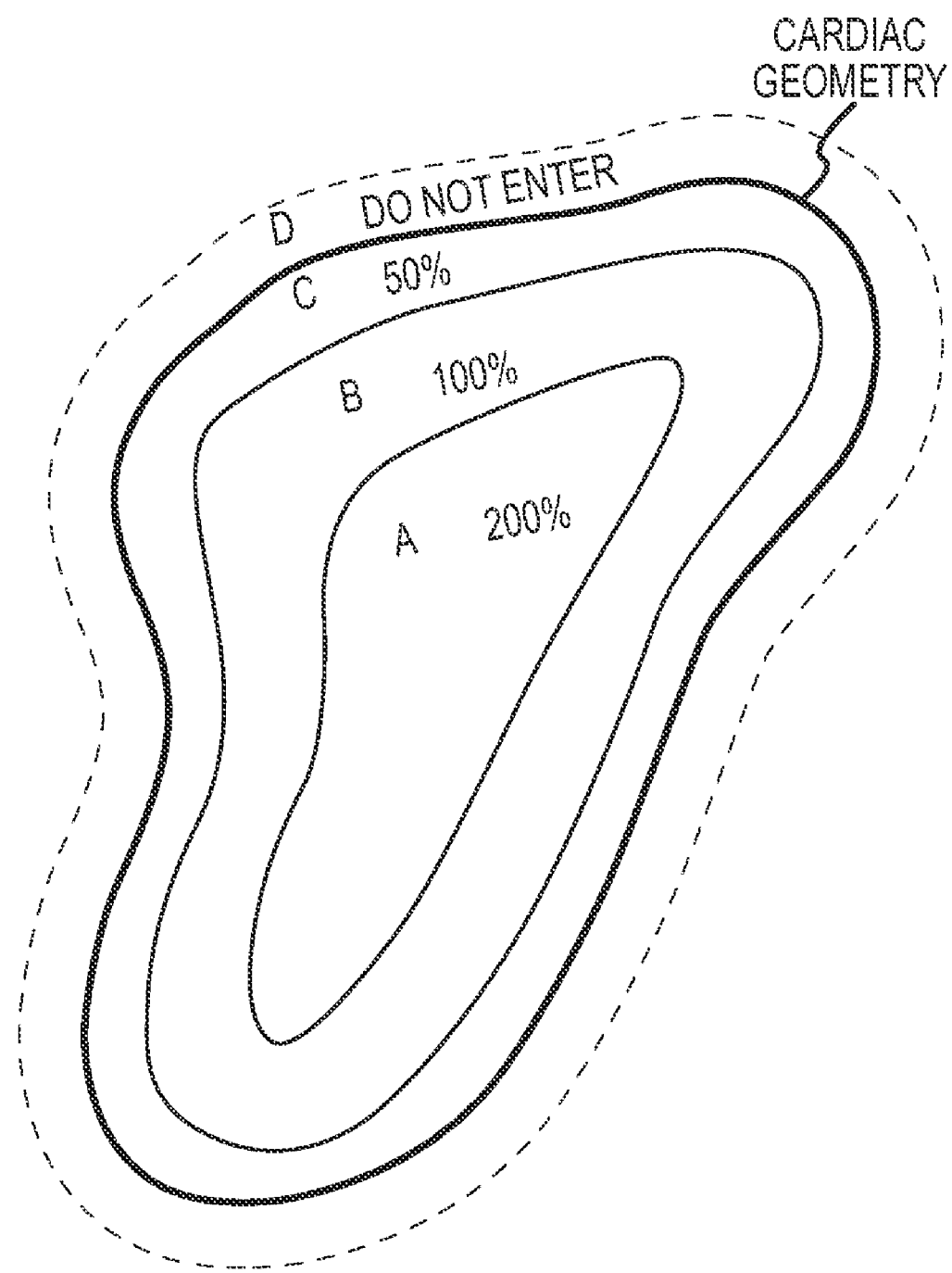
FIG. 10 is an exemplary view of speed-zones for optimizing movement of a catheter tip.

Pre-defined catheter "speed zones" will now be briefly discussed with reference to FIG. 10.

To aid users in navigating a catheter safely, yet quickly, around a cardiac chamber, robotic catheter system 10 may employ pre-defined "speed zones" to optimize the movement of the catheter tip. As described in relation to FIG. 10, zone A may be defined as the most central, and safest area in the cardiac chamber. In zone A, the catheter tip could be sped up so that the catheter tip can traverse this area at a faster than normal rate, e.g., 200% of the input motion. As the user moves the catheter closer to the cardiac wall, he/she may desire enhanced precision rather than speed. Therefore, zones B and C may purposefully and gradually reduce the scaling factor between input motion and tip movement. Finally, the user may have the ability to define a region exterior to the geometry, e.g., zone D, into which the catheter is prevented from entering. Alternatively, this "exterior zone" may be modeled to provide a force that would "push" the catheter back into the acceptable area. Alternatively, the speed could be any continuous or non-continuous function of distance from the endocardial wall, generally monotonically increasing as a function of distance from the wall.

Additionally, a special zone around more sensitive tissue could be defined to further limit speed. The speed could also be defined to be dependent on direction. For example, motion tangential to the surface although in closer proximity could be allowed to traverse faster than perpendicular to the tissue. Further, speed away from or moving away from the tissue could be allowed to be faster than speed towards tissue.

Haptic feedback system 900 may be integrated with user interface device 902 such that in zones A, B, and C, the dampening force on the handle of device 902 may change (e.g., as the catheter tip moves closer to the wall, the user might feel as if the tip is caught in an increasingly dense sludge). Once the tip starts to cross the barrier between zone C and zone D, this feeling may be accompanied by a force that prevents inadvertent continued motion.

The invention thus provides greater safety and efficacy to the practice of catheter electrophysiology by providing enhanced information to the cardiac electrophysiologists and in a way that is the most intuitive. The invention also provides a system and method for precise and dynamic automated control of a catheter and its related components, for example, for diagnostic, therapeutic, mapping and ablative procedures, that will provide haptic feedback to a user in a variety of predetermined or user-specific forms.

Those skilled in the art would appreciate in view of this disclosure that although haptic feedback system 900 has been described in conjunction with robotic catheter system 10, haptic feedback system 900 may be likewise used with a manual catheter. For example, instead of heating or cooling user interface 902, ablation energy may be fed back to the user in a manual catheter by heating the grip. Alternatively, the tissue sensing discussed in commonly owned and copending applications titled "System and Method for Measuring Force and Torque Applied to a Catheter Electrode Tip," and "Optic-Based Contact Sensing Assembly and System," may be relayed back to the user via a vibration motor in the catheter handle, or by likewise heating or cooling the grip.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A haptic feedback system for a robotic catheter system including a robotic catheter manipulator assembly including at least one removably mounted robotic catheter device cartridge and robotic sheath device cartridge, each cartridge being generally linearly movable relative to the robotic catheter manipulator assembly, the haptic feedback system comprising:
   a user interface device for controlling an operation associated with at least one of the catheter and sheath device cartridges; and
   a control system for evaluating at least one of a predetermined and a measured operational parameter of the haptic feedback system,
   wherein the user interface device provides haptic feedback to a user based on the evaluation by the control system,
   wherein the haptic feedback is user selectable.

2. The haptic feedback system according to claim 1, wherein the user interface device is at least one of an instrumented catheter handle control, an oversized catheter model, a user-wearable glove, a joystick, and a haptic spaceball.

3. The haptic feedback system according to claim 1, wherein the operational parameter includes at least one of a type, attachment, detachment, speed of movement, and axial and angular positions of at least one of the catheter and sheath device cartridges relative to the manipulator assembly.

4. The haptic feedback system according to claim 1, wherein the user interface device is operatively connected to a catheter and sheath respectively connected to the catheter and sheath device cartridges.

5. The haptic feedback system according to claim 4, wherein the operational parameter includes at least one of a speed of movement, force, proximity, angle of attack and rotational orientation of at least one of the catheter and sheath relative to an endocardial wall.

6. The haptic feedback system according to claim 5, wherein the endocardial wall is computer generated.

7. The haptic feedback system according to claim 4, wherein the operational parameter includes a tension of a steering wire for manipulating at least one of the catheter and sheath.

8. The haptic feedback system according to claim 4, wherein the operational parameter includes at least one of a temperature and texture of an endocardial wall relative to at least one of the catheter and sheath.

9. The haptic feedback system according to claim 1, wherein the user interface device is configured to provide at least one of virtual and augmented haptic feedback.

10. The haptic feedback system according to claim 9, wherein the virtual feedback directly correlates to the operational parameter.

11. The haptic feedback system according to claim 9, wherein the augmented feedback indirectly correlates to the operational parameter.

12. The haptic feedback system according to claim 1, wherein the haptic feedback includes at least one of active resistance, active push, active pull, vibration, and temperature variation of the user interface device.

13. The haptic feedback system according to claim 1, wherein at least one of a haptic type, mode and proportionality of the haptic feedback is user selectable.

14. A haptic feedback system for a robotic catheter system including a robotic catheter manipulator assembly including at least one removably mounted robotic catheter device cartridge and robotic sheath device cartridge, each cartridge being movable relative to the robotic catheter manipulator assembly, the haptic feedback system comprising:
   a user interface device for controlling an operation of the robotic catheter system; and
   a control system for evaluating at least one of a predetermined and a measured operational parameter of the haptic feedback system,
   wherein the user interface device provides haptic feedback to a user based on the evaluation by the control system,
   wherein the operational parameter includes at least one of a type, attachment, detachment, speed of movement, and axial and angular positions of at least one of the catheter and sheath device cartridges relative to the manipulator assembly.

15. The haptic feedback system according to claim 14, wherein the user interface device is at least one of an instrumented catheter handle control, an oversized catheter model, a user-wearable glove, and a joystick.

16. The haptic feedback system according to claim 14, wherein the user interface device is operatively connected to a catheter and sheath respectively connected to the catheter and sheath device cartridges.

17. The haptic feedback system according to claim 16, wherein the operational parameter includes at least one of a speed of movement, force, proximity, angle of attack and rotational orientation of at least one of the catheter and sheath relative to an endocardial wall.

18. The haptic feedback system according to claim 17, wherein the endocardial wall is computer generated.

19. The haptic feedback system according to claim 16, wherein the operational parameter includes at least one of a temperature and texture of an endocardial wall relative to at least one of the catheter and sheath.

20. The haptic feedback system according to claim 14, wherein the user interface device is configured to provide at least one of virtual and augmented haptic feedback.

21. The haptic feedback system according to claim 20, wherein the virtual feedback directly correlates to the operational parameter.

22. The haptic feedback system according to claim 20, wherein the augmented feedback indirectly correlates to the operational parameter.

23. The haptic feedback system according to claim 14, wherein the haptic feedback includes at least one of active resistance, active push, active pull, vibration, and temperature variation of the user interface device.

24. The haptic feedback system according to claim 14, wherein the haptic feedback is user selectable.

25. A method of providing haptic feedback for a robotic catheter system including a robotic catheter manipulator assembly including at least one removably mounted robotic catheter device cartridge and robotic sheath device cartridge, each cartridge being generally linearly movable relative to the robotic catheter manipulator assembly, the method comprising:

controlling an operation associated with at least one of the catheter and sheath device cartridges;

evaluating at least one of a predetermined and a measured operational parameter of the robotic catheter system; and providing haptic feedback to a user based on the evaluation, wherein the operational parameter includes a tension of a steering wire for manipulating at least one of a catheter coupled with said catheter device cartridge and a sheath coupled with said sheath device cartridge.

26. The method according to claim 25, wherein the operational parameter includes at least one of a type, attachment, detachment, speed of movement, and axial and angular positions of at least one of the catheter and sheath device cartridges relative to the manipulator assembly.

27. The method according to claim 25, wherein the operational parameter includes at least one of a speed of movement, force, proximity, angle of attack and rotational orientation of at least one of a catheter and sheath, respectively connected to the catheter and sheath device cartridges, relative to an endocardial wall.

28. The method according to claim 27, wherein the endocardial wall is computer generated.

29. The method according to claim 25, wherein the operational parameter includes at least one of a temperature and texture of an endocardial wall relative to at least one of a catheter and sheath respectively connected to the catheter and sheath device cartridges.

30. The method according to claim 25, further comprising providing at least one of virtual and augmented haptic feedback.

31. The method according to claim 30, wherein the virtual feedback directly correlates to the operational parameter.

32. The method according to claim 30, wherein the augmented feedback indirectly correlates to the operational parameter.

33. The method according to claim 25, wherein the haptic feedback is user selectable.

* * * * *